(12) United States Patent
Hofmann

(10) Patent No.: US 7,096,886 B2
(45) Date of Patent: Aug. 29, 2006

(54) MULTIPORT SWITCHING VALVE FOR A LIQUID FLOW SYSTEM

(75) Inventor: Martin Hofmann, Rheinstette (DE)

(73) Assignee: Brucker BioSpin GmbH, Rheinstetten-Forchheim (DE)

( * ) Notice: Subject to any disclaimer, the term of this patent is extended or adjusted under 35 U.S.C. 154(b) by 141 days.

(21) Appl. No.: 10/650,111

(22) Filed: Aug. 26, 2003

(65) Prior Publication Data
US 2004/0112444 A1    Jun. 17, 2004

(30) Foreign Application Priority Data
Aug. 30, 2002 (EP) .................. 02019400

(51) Int. Cl.
*F16K 11/072* (2006.01)
(52) U.S. Cl. .................. 137/625.46; 137/312
(58) Field of Classification Search ........... 137/625.46, 137/625.47, 595, 597, 312; 73/864.83
See application file for complete search history.

(56) References Cited

U.S. PATENT DOCUMENTS

| | | | | |
|---|---|---|---|---|
| 3,451,428 A | * | 6/1969 | Pruett | .................. 137/625.46 |
| 3,477,207 A | * | 11/1969 | Auger | .................. 96/104 |
| 3,800,602 A | | 4/1974 | Jones | |
| 4,133,640 A | | 1/1979 | Clinton et al. | |
| 4,923,616 A | | 5/1990 | Hirata et al. | |
| 5,193,581 A | * | 3/1993 | Shiroto et al. | ......... 137/625.11 |
| 5,270,212 A | * | 12/1993 | Horiuchi et al. | .............. 436/45 |
| 6,155,123 A | | 12/2000 | Bakalyar | |

FOREIGN PATENT DOCUMENTS

| | | |
|---|---|---|
| EP | 1 202 054 A1 | 5/2002 |
| WO | WO 01/94909 A1 | 12/2001 |

OTHER PUBLICATIONS

"Replacement Rotor Seals and Stators", RHEYODYNE, Catalog 2000, p. 18, et seq.

* cited by examiner

*Primary Examiner*—John Fox
(74) *Attorney, Agent, or Firm*—Kudirka & Jobse, LLP (57) ABSTRACT

A multiport switching valve for a liquid flow system is described, comprising a first member having a plurality of ports for connecting liquid lines thereto, a second member, connected with a first member and movable relative to the first member, the second member comprising a plurality of channels, wherein the channels are arranged such that, according to a selected relative position between the first and second member, one or more of said channel connect predetermined ones of the ports of the first member with one another in a liquid conducting manner. The first member comprises at least one group of ports arranged in one substantially straight line or at least two adjacent substantially parallel and substantially straight lines, and the second member comprises a plurality of segments, wherein the segments have one or more channels arranged therein, the channel or channels of each segment representing a predetermined connection scheme for connecting predetermined ones of the ports with one another.

17 Claims, 6 Drawing Sheets

MULTIPORT SWITCHING VALVE FOR A LIQUID FLOW SYSTEM

CROSS REFERENCE TO FOREIGN APPLICANT

The present application claims priority of European patent application 02 019 400.7 filed on Aug. 30, 2002.

BACKGROUND OF THE INVENTION

The invention relates to a multiport switching valve for a liquid flow system.

A valve of the afore-mentioned kind is, for example, known from the US-firm brochure of the company Rheodyne, Catalogue 2000—Injectors, Switching Valves, Fittings, Accessories, page 18.

Such a valve is used in all kinds of liquid handling systems, in particular in chromatography systems. Liquid chromatography is a known method for separating components of trace elements within liquid substrates to be analyzed. For example, in a liquid chromatography (LC)-nuclear magnetic resonance (NMR) system, a chromatography flow coming from a LC separating unit or a peak sampling or trapping unit, is fed to a first decision detector unit and subsequently to a NMR destination detector unit.

For the technique of LC-NMR four automation modes are known, as they are "on-flow", "stopped-flow", "time-slicing" and "loop-sampling".

In a pure on-line coupling, the NMR detector is directly coupled with the liquid chromatograph. In this on-line mode the separated peaks are fed from the LC continuously into the NMR detector to be spectromatically examined on-line therein.

As an alternative to the on-line mode the stopped-flow technique is used, when the flow pump of the LC is stopped as long as a component is investigated inside the NMR detector.

The peak-sampling mode is a mode in which single separated peaks coming from the LC are selected and intermediately stored in a peak-sampling unit for later investigation in the NMR detector.

The time-slicing mode is a clocked mode in which the LC peaks can be investigated in equally timed fractions to observe spectroscopic changes over a certain elusion period.

A LC-NMR system can additionally be hyphenated with a mass spectrometer (MS) leading to just a higher complexity of the system.

A valve of the kind mentioned at the outset is used in the afore-mentioned system in order to switch between the different functions of the system. However, the conventional known valves are restricted in view of their functionality so that usually more than one valve of the conventional design has to be used in order to be able to switch between all the functions of the liquid system. The conventional design of a valve of the kind mentioned at the outset will now be described with reference to FIGS. 9 through 12 of the accompanying drawings.

Figures 9, 10, 11:
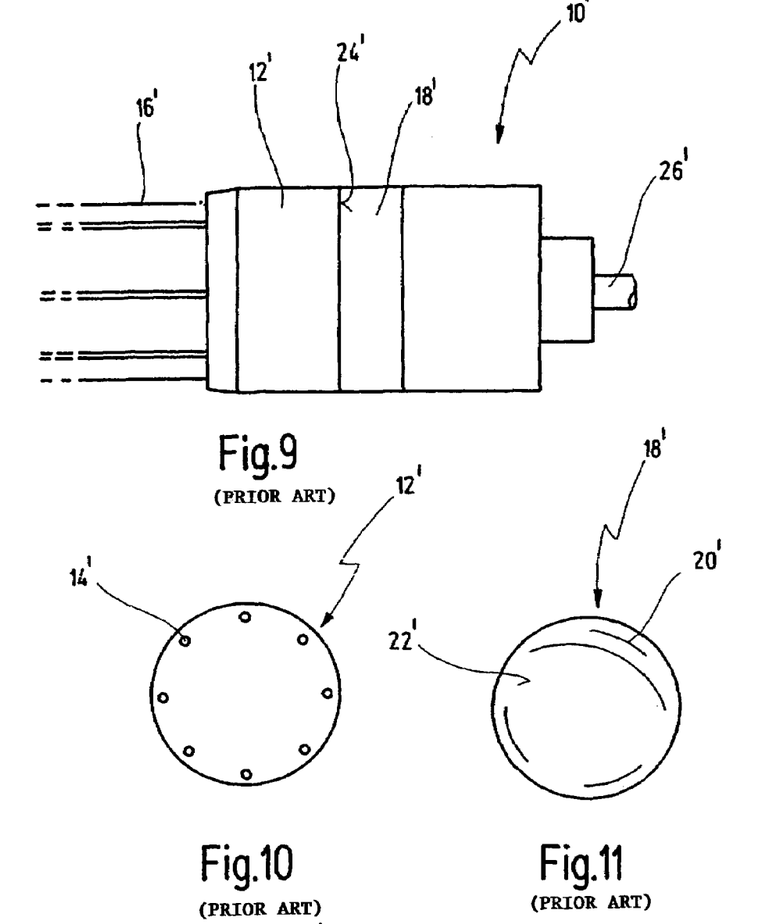
FIG. 9 shows a valve according to the prior art in a side view.
FIG. 10 shows a first member of the valve in FIG. 10 in a front view.
FIG. 11 shows a second member of the valve in FIG. 10 in a front view.

The conventional valves available on the market, which are designed as rotary valves, are constructed all in a similar way. In FIG. 9, there is shown a valve 10' configured as an eight-port rotary valve. The valve 10' comprises a First member 12' referred to as a stator having a plurality of ports 14', e.g. eight in the shown example (confer FIG. 10). The ports 14' are circumferentially distributed in a circular line about the center of the first member 12' in equal angular intervals. Eight liquid lines 16' can be connected to the ports 14', accordingly.

Figure 12:
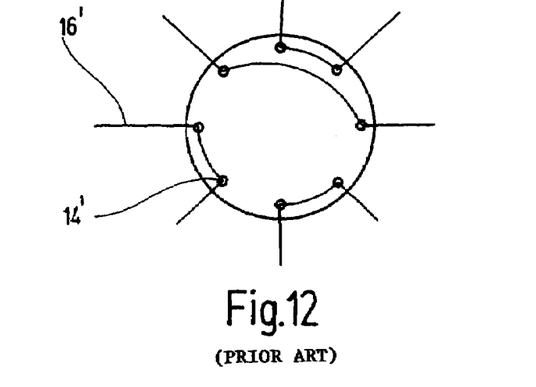
FIG. 12 schematically shows one switching position of the valve in FIG. 10.

A second member 18' is connected with the first member 12' and is movable relative to the first member 12'. The second member 18' is usually referred to as the rotor. The second member 18' which is shown in isolation in FIG. 11, comprises a plurality of channels 20' arranged on the surface of second member 20' which faces the rear surface of first member 12'. The channels 20' are, for example, configured as grooves edged in the surface 22' of second member 18'. The channels 20' are arranged such that, according to a selected relative position between the first and second member 12', 18', one ore more of said channels 20' connect predetermined ports 14' of the first member 12' with one another. One selected relative position is shown in FIG. 12. By rotating the second member 18' relative to the first member 12', for example by means of an external driving unit (not shown) via a shaft 26', another relative position between the first and second member 12', 18' can be obtained in order to connect other predetermined ports 14' than as shown in FIG. 12.

Such a design of a valve implies that a number of four or more valves can be necessary for a complex hyphenated LC-NMR system as described above, resulting in a high cost. A further disadvantage is that a large number of valves results in a high dead volume which is detrimental in LC systems where large dead volume affects the accuracy of the analysis.

U.S. Pat. No. 4,923,616 discloses a switching control valve. The known switching control valve comprises a stationary disk as the first member having concentric paths coaxially arranged at suitable intervals about the center of the stationary disk and having downward opening channels, a first group of vertical paths annularly arranged at regular intervals in the circumferential direction with a larger radius than those of the concentric paths and serving as downward opening channels, and a second group of vertical paths annularly arranged at regular intervals in the circumferential direction with a larger radius than that of the circle of the first group and serving as downward opening channels to form a number of counterparts corresponding to the vertical paths of the first group. The valve further comprises as the second member a rotary disk having junction paths comprising first junction paths arranged at suitable positions corresponding to the positions at which the vertical paths of the first and second groups are formed in the stationary disk.

Another multiport switching valve is known from U.S. Pat. No. 3,800,602. That valve comprises an eight port valve block, having a single channel and having a movable valve plate member slidably affixed thereto by a valve plate carrier which in a first position permits simultaneous sampling of a gas stream to be analyzed and back flushing of the chromatograph column and in a second position rapid analysis of the gas sample. By the addition of one or more six port programming valves or equivalent sampling means in series with the eight port valve, the apparatus may function to rapidly analyze two or more separate gas streams.

It is an object of the present invention to provide a multiport switching valve of the kind mentioned at the outset which has an increased functionality so that the number of valves for a complex liquid flow system can be reduced preferably to one valve which can fulfill all requirements of the system.

SUMMARY OF THE INVENTION

According to the invention, a multiport switching valve for a liquid flow system is provided, comprising:
- a first member having a plurality of ports for connecting liquid lines thereto;
- a second member connected with said first member and movable relative to said first member, said second member comprising a plurality of channels, wherein said channels are arranged such that, according to a selected relative position between said first and second member, said channels connect predetermined ones of said ports of said first member with one another in a liquid conducting manner, wherein said first member comprises at least one group of ports forming a substantially straight arrangement of ports, and said second member comprises a plurality of individual segments having at least one of said channels arranged therein, such that said at least one channel of each individual segment represents a predetermined connection scheme for connecting predetermined ones of said ports of said at least one group of ports only, with one another.

Instead of arranging the ports, for example eight ports in a circular line about the center of the first member and distribute these ports over the entire circumference of the first member, the first member of the valve according to the invention comprises at least one group of ports, for example eight ports arranged in one substantially straight line or at least two adjacent substantially parallel and substantially straight lines. This makes it possible, as it is also provided by the present invention, to use the second member more efficiently for a large number of channels by dividing the second member in a plurality of segments, wherein each segment defines a predetermined connection scheme for connecting predetermined ports of one and the same group of ports only, i.e. only such ports which form together a substantially straight arrangement with one another, according to the specific arrangement of the channel or channels in each segment, i.e. according to a predetermined pattern of the channel or channels in each segment. In other words, all the ports to be connected with one another form a substantially straight arrangement.

Preferably, there is at least one group of ports having at least three, preferably more than three ports forming a substantially straight arrangement of ports. For a valve of conventional size and rotary design it is possible to provide at least twelve such segments. On the first member the ports can be arranged in one substantially straight line or, in a more space saving manner, in at least two substantially parallel and substantially straight lines, in particular when the valve has a rotational design. The valve according to the invention has an increased functionality, and, when used in a complex liquid system, like LC-NMR or LC-NMR, it is possible to obtain all functions of the system with one valve only.

In a preferred configuration, the first member has a circular shape, and the at least one line of ports is directed substantially in radial direction with respect to the center of the first element.

This configuration is in particular advantageous with a rotational design of the valve, and it makes it possible to configure the segments having the channel or channels therein as sectors of a circle, as provided in another preferred configuration, resulting in an optimal exploitation of the size of the second member in case of a rotational design in order to obtain a maximum number of connection schemes and, therefore, functions of the valve.

In a design of the valve according to the invention with rotational symmetry it is further preferred if the second member is rotatable about its center axis relative to the first member.

In an alternative configuration, it can be preferred if the second member is configured as a translational slider, and the segments are arranged in parallel with one another.

This configuration can be envisaged in case that there are no restrictions as to the size of the valve, wherein the number of parallel segments and therefore connection schemes represented by the channel or channels of each segment, is practically within the free choice of the user.

In a further preferred configuration the first member comprises at least two groups of ports, each group having the ports arranged in one substantially straight line or at least two substantially parallel and substantially straight lines, wherein the ports of the at least one second group form an arrangement substantially identical to the ports of the first group.

This configuration has the advantage that the at least one second group of ports will allow to access the channels of the second member for cleaning purposes.

In connection with a circular shape of the first and second member as mentioned before, it is further preferred if the at least two groups of ports are arranged circumferentially offset with respect to each other, preferably opposite to each other with respect to the center of the first member.

This configuration, which is provided in connection with a rotational design of the valve, has besides the advantage that there are additional connection ports on the first member which could advantageously be used to clean the pathway of the valve or to add further liquids for a latter use in the system in which the valve is incorporated, the additional advantage of a symmetrical arrangement of the ports which avoids additional stress on the seal between the first member and the second member due to a more symmetric sealing structure rendered possible in this configuration.

In a further preferred configuration the segments of the second member are divided from each other by separation channels leading to a common liquid outlet.

This feature has the particular advantage that liquid cannot enter from one segment into other segments in case of leakages, i.e. the liquid carry-over effect between two segments or two switching positions of the valve is avoided or at least reduced.

In case of a rotational design of the second member, the afore-mentioned outlet is disposed in the center of the second member and communicates with an outlet port provided on the first member.

This has the advantage that in case of a leakage the liquid is drained to a predetermined fixed location of the valve.

In this connection it is further preferred, if a sensor for detecting liquid is arranged at the outlet port.

This feature has the advantage that leakages and malfunctions can be detected by the sensor very quickly, and the system can be stopped in case of a malfunction in due time.

In a further preferred configuration the channels of each segment are arranged in the same plane.

In this case an axially short construction of the second member, which can be configured as a chip having the channels edged therein, is achieved.

When it is desired to have the third dimension of the second member to be used in order to further enhance the functionality of the valve, in particular to combine the connection schemes of two or more segments with each other, it can be preferably provided that the channels are arranged in at least two different planes, and/or tunneling channels can be provided to connect channels of different segments with each other, without having the liquid carry-over problem due to crossing channels.

Further features and advantages will be apparent from the following description and the attached drawings.

It will be understood that the above-mentioned features and those to be discussed below, are not only applicable in the given combinations, but may also be employed in other combinations or taken alone without departing from the scope of the present invention.

BRIEF DESCRIPTION OF THE DRAWINGS

Exemplary embodiments of the present invention are illustrated in the drawings and will be discussed in more detail below. In the drawings.

DETAILDED DESCRIPTION OF PREFERRED EMBODIMENTS

Figure 1:
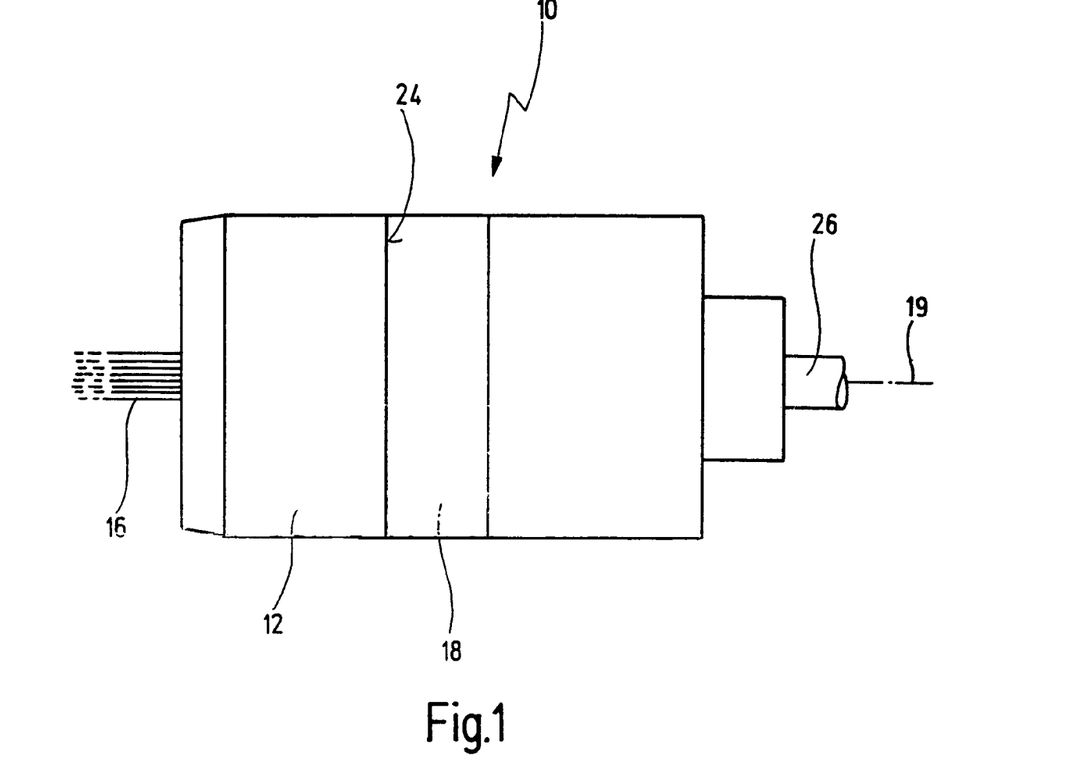
FIG. 1 shows a valve in a side view.
Figure 2:
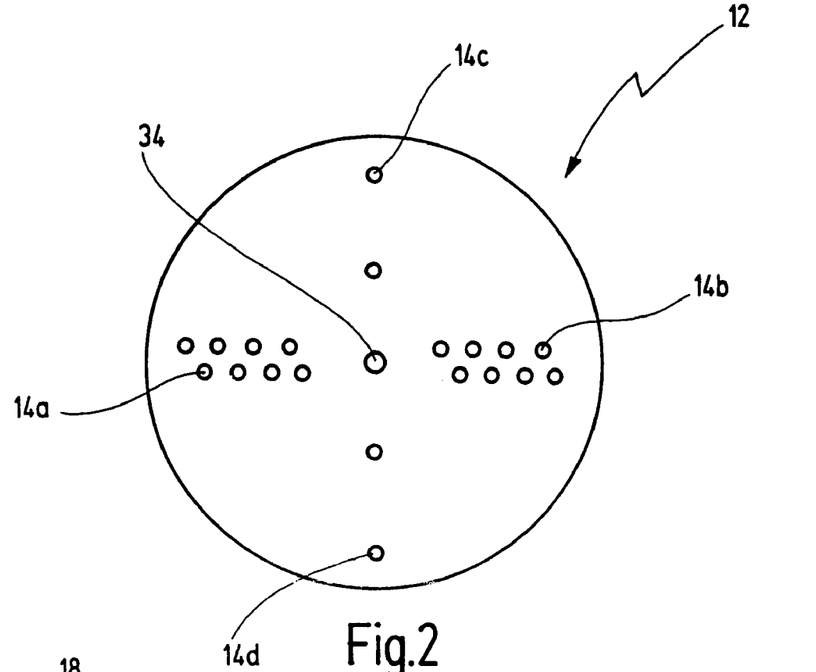
FIG. 2 shows a first member of the valve in FIG. 1 in a front view.
Figure 3:
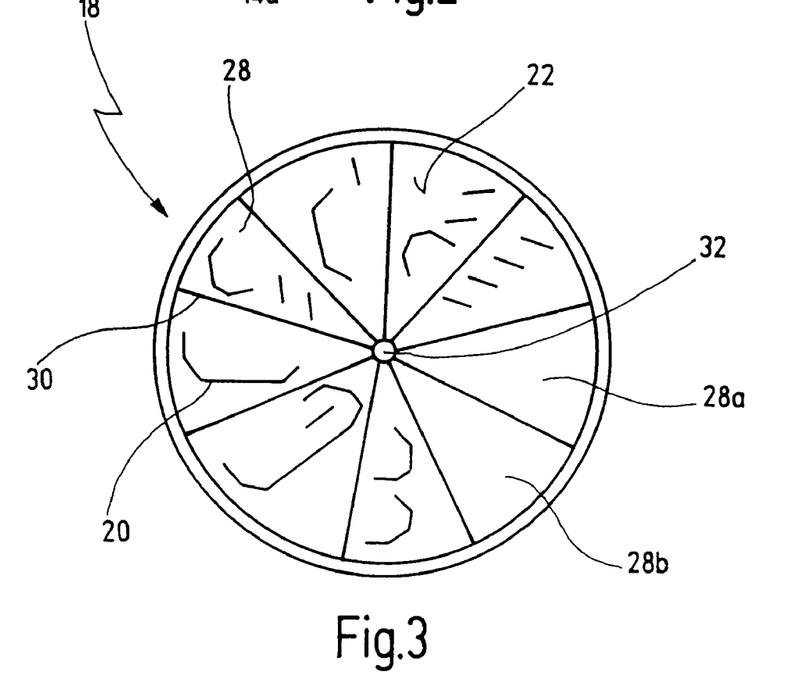
FIG. 3 shows a second member of the valve in FIG. 1 in isolation in a front view.

In FIG. 1, a multiport switching valve for a liquid flow system which is generally labeled in its entirety with reference numeral 10, is shown. FIGS. 2 and 3 show further details of valve 10.

The valve 10 is used in a liquid handling system, for example a LC system hyphenated with a NMR detector, as will be described later.

The valve 10 generally has a rotational design. The valve 10 comprises a first member 12 which is stationary and can be referred to as stator.

The first member 12 comprises a plurality of ports labeled in their entirety with 14a, 14b, 14c and 14d, as shown in FIG. 2. Liquid lines labeled in their entirety with 16, for example capillary lines, which lead liquid to and from the valve 10, can be connected to the ports 14a. It is to be understood that further liquid lines (not shown) can be connected to the ports 14b, 14c and/or 14d depending on the specific application of the valve 10.

The valve 10 further comprises a second member 18, which is connected with the first member 12 and movable relative to the first member 12. In the present embodiment, the second member 18 is rotatable about its center axis 19 relative to the first member 12, wherein the second member 18 is driven by an external driving unit (not shown) via a shaft 26.

The second member 18 is sealed with the first member 12 in a liquid tight manner.

The second member 18 comprises a plurality of channels labeled in their entirety with 20 (FIG. 2), which, for example, are grooves edged into a surface 22 facing a surface 24 (FIG. 1) of the first member 12, to which the ports 14a, 14b, 14c, 14d open.

In difference to the conventional valve design which has already been described in the introductory portion of the present application with respect to FIGS. 9 through 12, the group of the eight ports 14a are arranged in two substantially parallel and substantially straight lines. In the embodiment shown, the first member 12 has a circular shape and the two lines of ports 14a are directed substantially in radial direction with respect to the center of the first member 12. The eight ports 14b form a second group of ports which are also arranged in two substantially parallel and substantially straight lines. The group of ports 14b is arranged opposite to the group of ports 14a with respect to the center of the first member 12. The group of ports 14b is arranged identical to the group of ports 14a. The two ports 14c form a third group of ports, and the two ports 14d form a fourth group of ports, wherein the ports 14c and 14d are arranged opposite to each other, and are circumferentially offset by about 90° with respect to the ports 14a and 14b. This is done to achieve the most compact design and to reduce the entire surface to get a better sealing.

Further in difference to the conventional valve design, the second member 18 comprises a plurality of segments labeled in their entirety with 28, the number of which is nine in the present embodiment as shown in FIG. 3. The number of segments 28 is not critical, and with usual dimensions and sizes of the valve 10 it is possible to provide twelve or even more such segments on the second member 18 without difficulty.

Each segment 28 comprises one or more of the channels 20, wherein the pattern or configuration of the channels 20 differ from segment to segment. The channel or channels of each segment 28 represents or represent a predetermined connection scheme for connecting predetermined ports of the same group of ports only, for example the ports 14a, with one another. In the embodiment shown in FIG. 3, there are two segments 28a and 28b, which do not comprise channels. However, these segments 28a and 28b can also comprise channels 20, for example for another function or other applications of the valve if desired.

The segments 28 are configured as sectors of the circle of the second member 18 which allows the most space saving arrangement and distribution of the segments 28 on the second member 18 for a rotational design. In the embodiment shown in FIGS. 1 through 3, all the channels 20 are arranged in the same plane, i.e. in the surface 22 of the second member 18. In the ideal case, the segment dimensions will be identical, but they could also vary, as shown in FIG. 3.

However, it could be envisaged to arrange the channels 20 in at least two different planes in order to use the three dimensionality of the second member 18 for a larger number of functions or connection schemes. It could also be envisaged to provide tunneling channels (not shown) connecting the channels 20 of different segments 28 with each other.

The segments 28 are separated from each other by separation channels 30 which lead to a common outlet 32 of the second member 18, which is in registry with an outlet port 34 regardless of the switching position of the valve 10, i.e. the relative position between the first member 12 and the second member 18. The separation channels 30 avoid a carry-over of liquid between adjacent ones of the segment 28. The outlet 32 is arranged in the center of the second member 18, and the outlet port 34 is arranged in the center of the first member 12, accordingly. It will be obvious to a skilled person that the drain port 32 could be also placed anywhere on the outer ring of the shown separation channels to fulfill the identical function. A sensor (not shown) for detecting liquid can be arranged at the outlet port 34 in order to detect leakage situations of the valve 10.

In the embodiment shown in FIG. 3, there are seven different connection schemes in seven segments 28 for connecting predetermined ports of the ports 14a, for example, with one another.

The pattern of the channel or channels 20 of each segment 28 is chosen according to the specific application of the valve 10 in a liquid handling system. The seven connection schemes according to the seven segments 28 of the second member 18 in FIG. 3 cannot be obtained by the design of the first and second members 12' and 18' of the valve 10' in FIGS. 11 and 12. In order to obtain the same connection schemes as in FIG. 3, it would be necessary to combine a number of at least four valves 10', whereas the seven connection schemes are now realized in one and the same valve 10.

Figure 4:
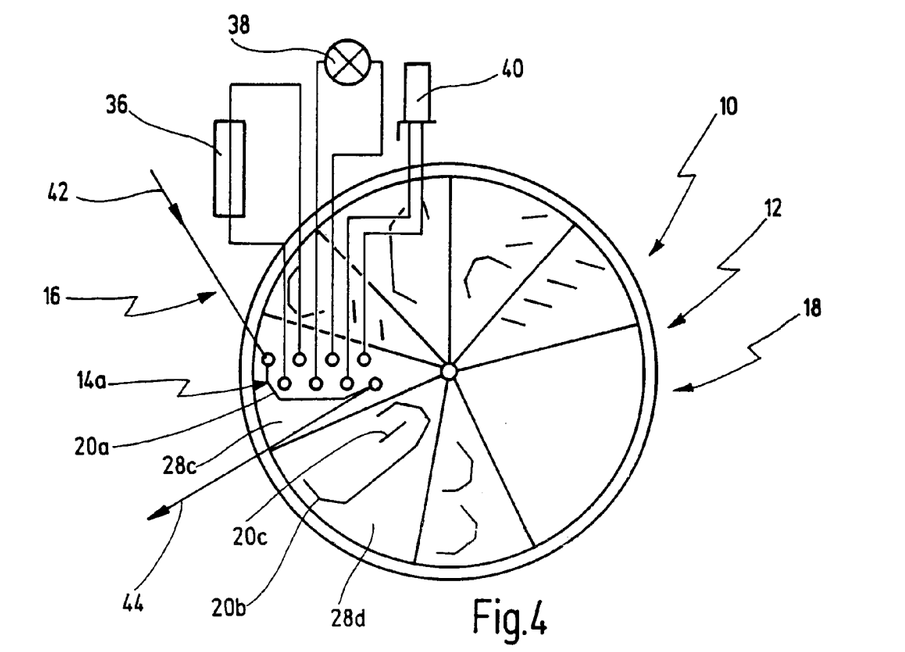
FIG. 4 shows a schematical representation of a possible application of the valve in FIG. 1 in a LC-NMR system, the valve being in a first switching position.
Figure 5:
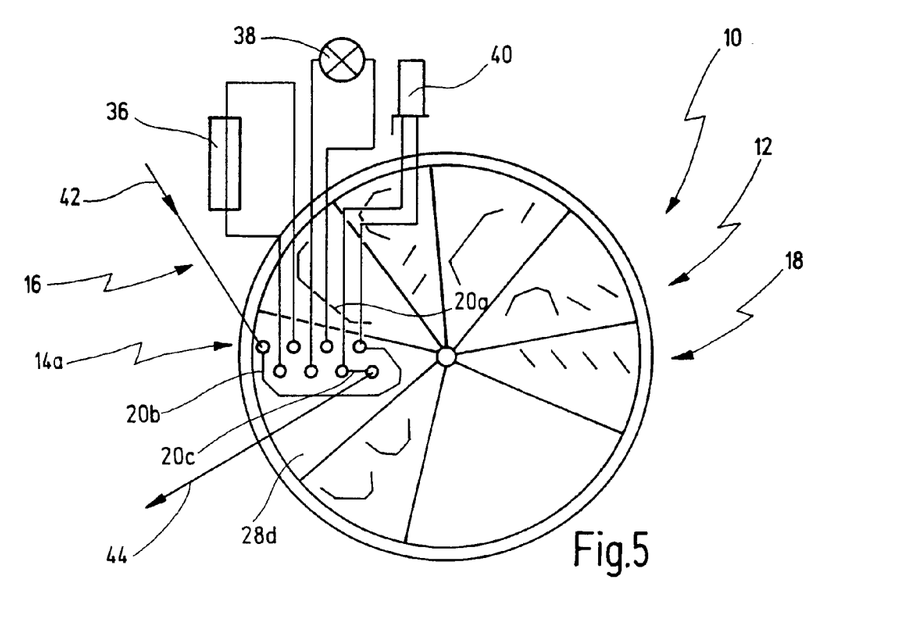
FIG. 5 shows the system in FIG. 4 in a second switching position of the valve.

With respect to FIGS. 4 and 5, an exemplary application of the valve 10 having the design of the second member 18 shown in FIG. 3 in a LC-NMR system is shown.

The system comprises a separation column 36, a chromatography detector 38, a NMR probe. 40, an injector represented by a line 42 and a waste represented by a line 44. Each of the afore-mentioned components of the system is connected via one or two liquid lines 16 with the ports 14a, wherein each line 16 is connected to a respective port 14a. Depending on the application and the valve size, even more ports will be possible. According to the number of eight lines 16, eight ports 14a are necessary in order to have each line 16 connected with one port 14a.

In FIG. 4, the valve 10 is shown in a switching position, where the channel 20a of the segment 28a is in registry with the one of the ports 14a, to which the injector 42 is connected, and with the one of the ports 14a, to which the waste 44 is connected. In this switching position of the valve 10, liquid is led from the injector 42 directly to the waste 44. The remaining ones of the ports 14a are not connected with one another so that there is no liquid flow through these ones of the ports 14a.

In FIG. 5, the same system as in FIG. 4 is shown, whereas the valve 10 has been switched into another switching position by rotating the second member 18 relative to the first member 12. in this switching position, the channels 20b and 20c or the segment 28d have been brought into registry with the ports 14a, wherein the channel 20b connects the one of the ports 14a to which the injector 42 is connected, with the one of the ports 14a, to which the outlet line of the NMR probe 40 is connected, and the channel 20c connects the one of the ports 14a to which the inlet line of the NMR probe 40 is connected with the one of the ports 14a, to which the waste is connected. In this switching position of the valve 10, liquid flows from the injector 42 through the valve 10 into the NMR probe 40 and from the NMR probe 40 through the valve 10 to the waste 44 in a back flushing mode.

The other five switching positions of the valve 10 will not be described here, because they will be apparent from FIGS. 4 and 5 for a person skilled in the art in a self-explaining manner.

Figure 6:
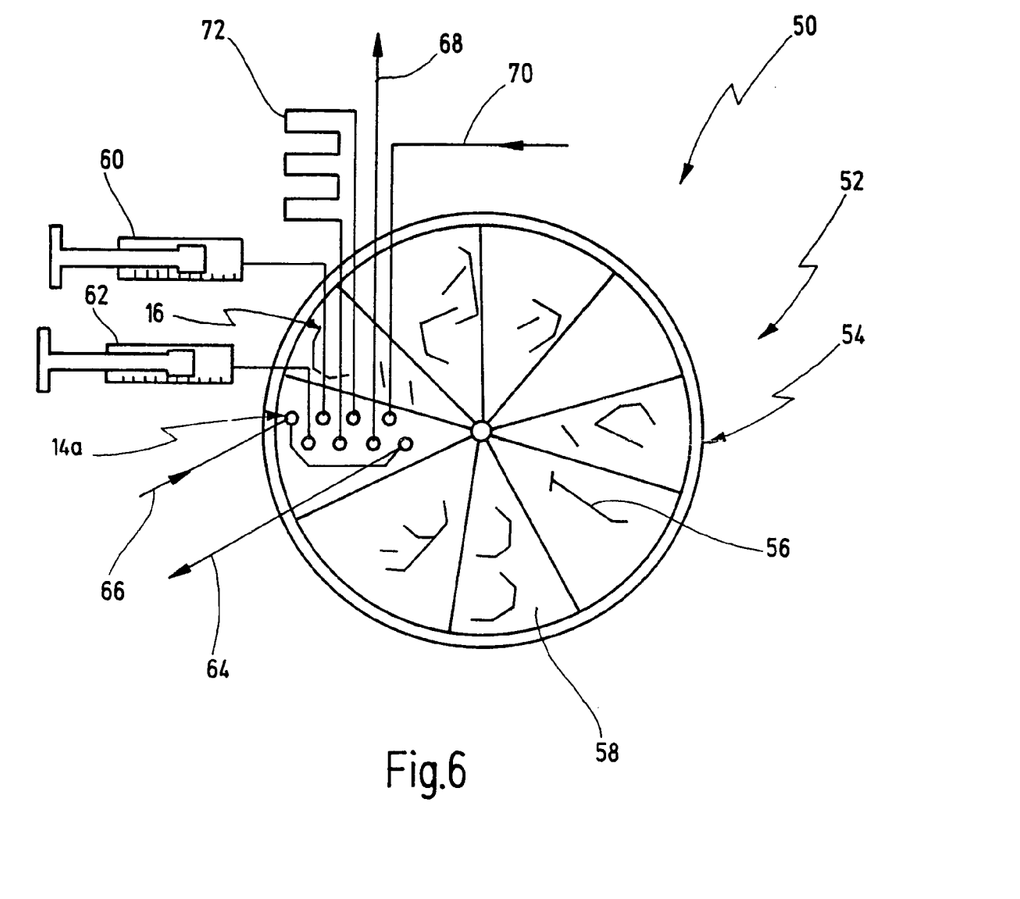
FIG. 6 shows a schematic representation of another valve used for example in a LC-MS system, the valve being in a selected switching position.

In FIG. 6 there is schematically shown another embodiment of a valve 50 in an exemplary application in another system than the system in FIGS. 4 and 5. In the following, only the differences between the valve 50 and the valve 10 are described.

The valve 50 comprises a first member 52 which can be of the same design as the first member 12 of valve 10. Accordingly, the first member 52 comprises at least the first group of ports 14a as shown in FIG. 2.

The valve 50 further comprises a second member 54 comprising channels 56 which are arranged in segments 58. There are nine segments in total, wherein eight of the segments 58 comprise one or more channels 56, according to eight different switching positions of the valve 50.

As can be seen by comparison of FIGS. 3 and 6, the pattern of the channels 56 differs from the pattern of the channels 20 of valve 10. The pattern of the channels 56, the channel or channels 56 of each segment 58 again defining a specific connection scheme for connecting predetermined ports of the ports 14a with one another, is chosen with respect to the application of the valve 50 in the system shown in FIG. 6.

The afore-mentioned system comprises a first pump 60 for dispensing a push solvent, a second pump 62 for dispensing an ionization solvent, a mass spectrometer (not shown) represented by a line 64, a chromatography splitter (not shown) represented by a line 66, a waste represented by a line 68, a flow injection device represented by a line 70 and a loop sampling unit 72. All the afore-mentioned components are connected to the ports 14a via lines labeled again in their entirety with reference numeral 16.

The pattern of the channels 56 has been chosen to obtain the required connections between the ports 14a in order to be able to perform all the functions of the system. In FIG. 6 the valve 50 is shown in a switching position in which the one of the ports 14a to which the chromatography splitter 66 is connected, is connected with the one of the ports 14a to which the mass spectrometer 64 is connected. In this position, liquid coming from the chromatography splitter 66 is directly fed into the mass spectrometer 64. Other functions of the system, i.e. other possible liquid flows in the system depending on the relative position between the first and second members 52 and 54, will become apparent to a person skilled in the art without further description being necessary.

Figures 7, 8:
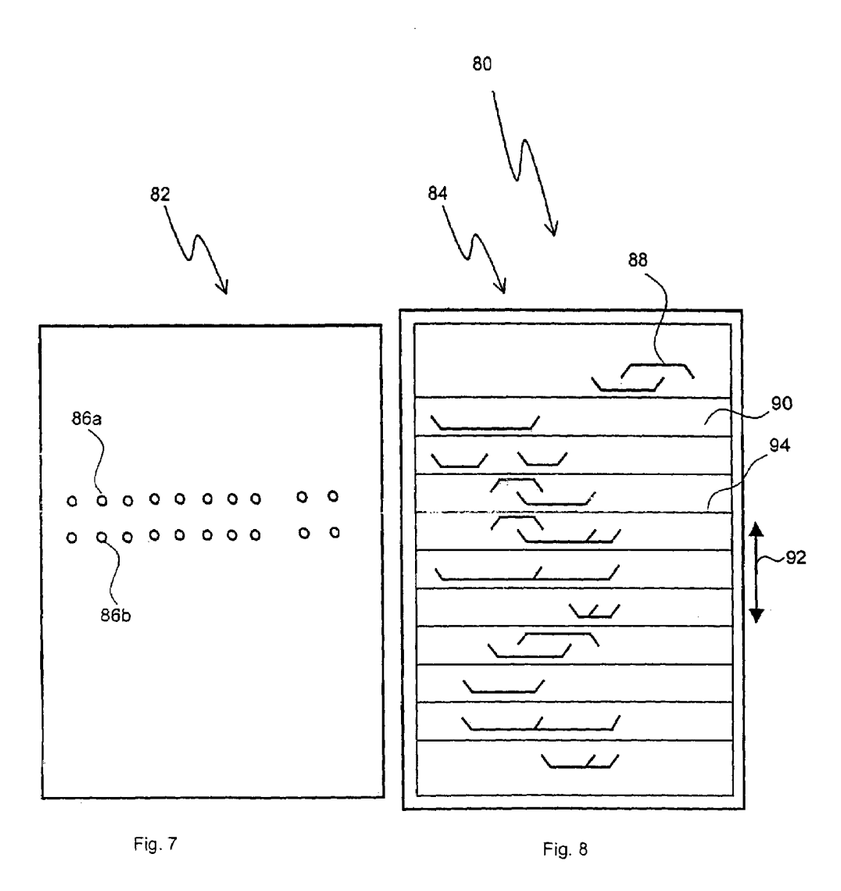
FIG. 7 shows a first member of a valve according to another embodiment.
FIG. 8 shows a second member to the first member in FIG. 7.

In FIGS. 7 and 8, another embodiment of a valve 80 is schematically shown comprising a first member 82 and a second member 84, wherein the first and second members 82 and 84 are shown one beside the other. It is, however, to be understood that the first member 82 is, in use, connected with the second member 84 in superimposed fashion.

The first member comprises a first group of ports 86a (in the present embodiment ten) and a second group of ports 86b which each are arranged in a substantially straight line, wherein the arrangement of the first and second group of ports 86a and 86b are identical to each other.

The second member 84 comprises channels 88 which are arranged in adjacent segments 90 which are arranged parallel with respect to each other. The second member 84 is configured as a translational slider which can be translationally moved relative to the first member 82 according to a double arrow 92. The second member 84 includes eleven segments 90 in total, each having at least one channel 88, corresponding to eleven different connection schemes in order to connect predetermined ports of the ports 86 with one another.

The segments 90 are separated from each other by separation channels 94 which avoid a carry-over of liquid between the segments 90.

The second group of ports 86b can be used to clean the channels 88 of the second member 84.

All the embodiments described before should be designed to assure high pressure stability for pressures up to 300 bar if used in chromatography systems. In other liquid handling systems, the valves should be able to stand 70 bar.

Further, it is to be understood that the examples of the design of the second members of the valves shown in the figures, in particular the pattern of the channels in the second member, are only exemplary, also the applications of the valves described above. It is also possible to design the second member to have segments with channels therein in a number and configuration such that one and the same valve can provide for two or more complete sets of connection schemes for two or more different applications of the valve in different systems.

What is claimed is:

1. A multiport switching valve for a liquid flow system, comprising:
    a first member having a plurality of ports for connecting liquid lines thereto;
    a second member connected with said first member and movable relative to said first member, said second member comprising a plurality of channels, wherein said channels are arranged such that, according to a selected relative position between said first and second member, said channels connect predetermined ones of said ports of said first member with one another in a liquid conducting manner,
    wherein said first member comprises at least one group of ports forming a substantially straight arrangement of ports, and said second member comprises a plurality of individual segments having at least one of said channels arranged therein and being divided from each other by separation channels leading to a common liquid outlet, such that said at least one channel of each individual segment represents a predetermined connection scheme for connecting predetermined ones of said ports of said at least one group of ports only, with one another.

2. The valve of claim 1, wherein said at least one group of ports comprises at least three ports.

3. The valve of claim 1, wherein said at least one group of ports comprises at least eight ports.

4. The valve of claim 1, wherein all ports of said at least one group of ports are arranged in one substantially straight line.

5. The valve of claim 1, wherein said ports of said at least one group of ports are arranged in at least two adjacent substantially parallel and substantially straight lines.

6. The valve of claim 1, wherein said first member has a circular shape, and said at least one group of ports is directed substantially in radial direction with respect to a center of said first element.

7. The valve of claim 1, wherein said second member has a circular shape, and said segments are configured as sectors of said second member.

8. The valve of claim 7, wherein said second member is rotatable about its center axis relative to said first member.

9. The valve of claim 1, wherein said second member is configured as a translational slider, and said segments are arranged in parallel with one another.

10. The valve of claim 1, wherein said first member comprises at least a second group of ports forming a substantially straight arrangement of ports, wherein said ports of said at least one second group form an arrangement substantially identical to said ports of said at least one group of ports.

11. The valve of claim 10, wherein said first member has a circular shape, and said at least one group of ports is directed substantially in radial direction with respect to a center of said first element, and wherein said at least one second group of ports is arranged circumferentially offset with respect to said at least one group of ports.

12. The valve of claim 11, wherein said at least one second group of ports is arranged opposite to said at least one group of ports with respect to said center of said first member.

13. The valve of claim 1, wherein said second member has a circular shape, and said segments are configured as sectors of said second member, and wherein said outlet is disposed in a center of said second member and communicates with an outlet port provided on said first member.

14. The valve of claim 1, wherein said common liquid outlet communicates with an outlet port provided on said first member, and wherein a sensor for detecting liquid is arranged at said outlet port.

15. The valve of claim 1, wherein said channels of each segment are arranged in a same plane.

16. The valve of claim 1, wherein said channels are arranged in at least two different planes.

17. The valves of claim 1, wherein tunneling channels are provided to connect channels of different segments with each other.

* * * * *